United States Patent
Van Baren et al.

(10) Patent No.: US 8,341,790 B2
(45) Date of Patent: Jan. 1, 2013

(54) DRIVE SYSTEM FOR A TOOTHBRUSH USING A FLEXIBLE MEMBRANE FOR CLEANING TEETH

(75) Inventors: Martijn Van Baren, Joure (NL); Klaas Kooijker, Drachten (NL); Wilhelmus Gerardus Maria Ettes, Leeuwarden (NL); Pawel Leshem, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 896 days.

(21) Appl. No.: 11/722,335

(22) PCT Filed: Dec. 20, 2005

(86) PCT No.: PCT/IB2005/054343
§ 371 (c)(1),
(2), (4) Date: Oct. 13, 2009

(87) PCT Pub. No.: WO2006/067749
PCT Pub. Date: Jun. 29, 2006

(65) Prior Publication Data
US 2011/0167575 A1    Jul. 14, 2011

Related U.S. Application Data

(60) Provisional application No. 60/638,058, filed on Dec. 21, 2004.

(51) Int. Cl.
*A61C 17/22* (2006.01)
(52) U.S. Cl. .......................................... 15/22.1; 15/22.2
(58) Field of Classification Search .................... 15/22.1
See application file for complete search history.

(56) References Cited

U.S. PATENT DOCUMENTS

| | | | |
|---|---|---|---|
| 3,631,556 A | 1/1972 | Holster et al. | |
| 4,162,576 A | 7/1979 | Takemoto et al. | |
| 4,346,492 A | 8/1982 | Solow | |
| 5,327,608 A * | 7/1994 | Kosakewich | 15/22.1 |
| 5,623,746 A * | 4/1997 | Ichiro | 15/22.2 |
| 2003/0115693 A1* | 6/2003 | Grez et al. | 15/22.1 |
| 2004/0010870 A1 | 1/2004 | McNair | |
| 2004/0130221 A1 | 7/2004 | Ichii et al. | |
| 2005/0283928 A1* | 12/2005 | Grez et al. | 15/22.1 |

FOREIGN PATENT DOCUMENTS

| | | |
|---|---|---|
| DE | 1995120 | 10/1968 |
| DE | 202005003515 | 6/2005 |
| DE | 202005003515 * | 7/2005 |
| WO | WO02082947 | 10/2002 |
| WO | WO2005000150 | 6/2005 |

* cited by examiner

*Primary Examiner* — Monica Carter
*Assistant Examiner* — Stephanie N Berry

(57) ABSTRACT

The power toothbrush includes a toothbrush body and a stem portion extending from the toothbrush body which has a workpiece with a flexible membrane at a remote end thereof, and a flexible membrane at a near end thereof as well. A movable piston is positioned in the stem portion, as well as a fluid which is in communication with the flexible membrane at the workpiece end of the toothbrush and the flexible membrane at the near end of the stem portion. The body includes a solenoid coil which, when actuated, moves the piston in opposing directions in a controlled manner within the stem, which acts on the fluid in the stem and moves the flexible membrane at the workpiece in and out at a desired frequency and amplitude.

8 Claims, 3 Drawing Sheets

DRIVE SYSTEM FOR A TOOTHBRUSH USING A FLEXIBLE MEMBRANE FOR CLEANING TEETH

CROSS REFERENCE TO RELATED APPLICATION

This application claims the benefit of U.S. provisional application Ser. No. 60/638,058 filed 21 Dec. 2004, which is incorporated herein by reference.

This invention relates generally to power toothbrushes, and more specifically to power toothbrushes which use a flexible membrane for cleaning teeth, including interdentally, and more particularly concerns a drive system for the flexible membrane of such a toothbrush.

Use of a flexible membrane in a brushhead portion of an oral cleaning device, such as a toothbrush, to achieve effective cleaning of teeth is shown in U.S. Patent Application Ser. No. 60/483,149, filed on Jun. 26, 2003, which is owned by the assignee of the present invention. The contents of the '149 application are hereby incorporated by reference. A variety of different structural arrangements can be used to drive the flexible membrane to produce a desired cleaning action, i.e. move the flexible membrane in and out relative to the remainder of the brushhead at a frequency and amplitude which produces the desired teeth cleaning.

In some cases, bristles can be mounted on the flexible membrane to assist in the cleaning process. However, such membrane-based toothbrushes do not require bristles for cleaning. While various drive system arrangements can be used, it is desirable that a drive system be both easy to manufacture and reliable in operation, as well as being inexpensive and capable of fitting into a conventional toothbrush structure.

Accordingly, the present invention is a power toothbrush, comprising a toothbrush body; a stem portion extending from the toothbrush body having a membrane workpiece at a remote end thereof and a membrane at a near end thereof as well; a piston assembly located in the stem portion and including a fluid therein which extends up to and is in contact with the membrane workpiece; and means for actuating the piston to move the fluid in the stem, causing at least a portion of the workpiece membrane to move outwardly when the piston moves in one direction and inwardly when the piston moves in the opposing direction.

The figures show several embodiments of a particular drive system for an oral care device using a flexible membrane to accomplish desired cleaning.

Figure 1:
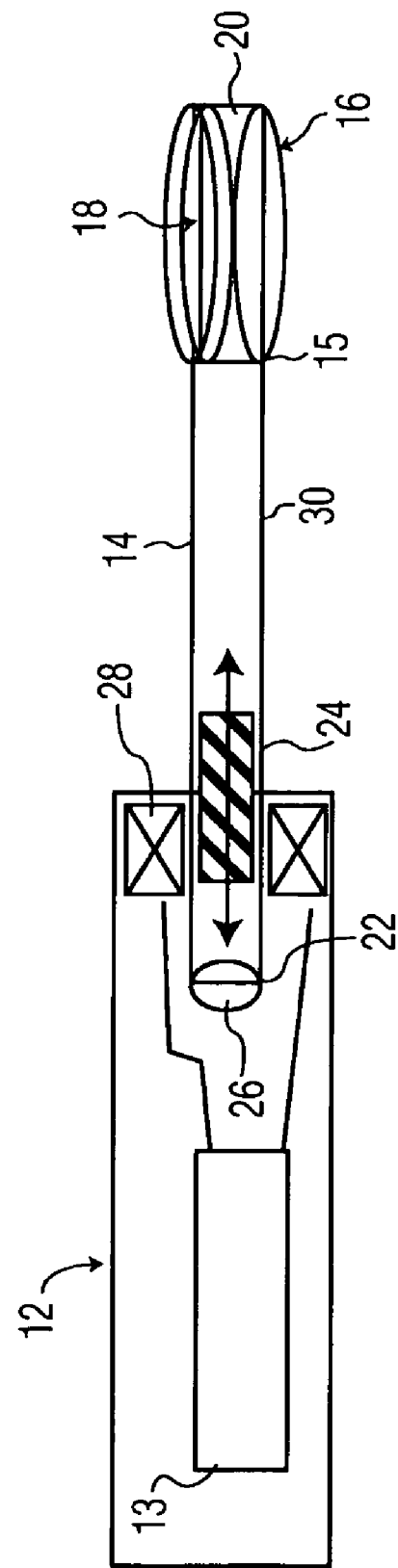
FIG. 1 is a simplified cross-sectional view of an oral care appliance which includes the membrane drive system of the present invention.

FIG. 1 shows one embodiment of the invention. A toothbrush body is shown representationally at 12. The toothbrush body will contain a battery and electronic control circuitry 13 for the toothbrush. Such elements are conventional and well known and, hence, are not described or shown in detail. Extending from the toothbrush body portion is a hollow toothbrush hollow stem 14. At a remote end 15 of stem 14 is a brushhead, shown generally at 16. Mounted in the brushhead 16 is a flexible membrane 18 which has a configuration (outline) suitable for cleaning teeth, i.e. similar to a brush configuration for toothbrushes. Behind membrane 18 within brushhead 16 is a volume 20 which is in fluid communication with hollow stem 14. Although there are no bristles shown mounted on membrane 18 in FIG. 1, it should be understood that bristles can be provided extending from the membrane 18, and or the brushhead itself, to assist in teeth cleaning.

Mounted within hollow stem 14 is a piston 24. Piston 24 is mounted to be movable in both directions within the hollow brush stem 14. The near end 22 of hollow stem 14, within the body of the toothbrush, also has a flexible membrane 26.

Extending around hollow stem 14 in the vicinity of piston 24 when it is at rest is a solenoid coil assembly 28. The hollow stem 14 extends sufficiently into body 12 that piston 24 is in electromagnetic relationship with the coil assembly, and moves under the influence of the coil assembly.

Coil assembly 28 can be configured with one or more coil portions or two separate coils, or one coil and a permanent magnet. Also, there could be more than two separate coils, permitting a programmability for the membrane action. In operation, with two separate coils or two coil portions, for instance, when piston 24 is moved in one direction by one portion of coil assembly 28, membrane 18 in brushhead 16 is pushed outwardly by piston 24 acting directly on fluid 30 contained within the toothbrush, hollow stem 14. The fluid composition can vary, as pointed out in the '149 application, including water, oil and other substances. Membrane 26 at the near end 72 of the toothbrush stem is moved inwardly (sucked in) by the same action of the piston on the fluid.

When the other coil portion or coil or the permanent magnet is energized, the piston moves in the opposing direction, with membrane 18 moving inwardly while membrane 26 is pushed outwardly from the near end 22 of hollow stem 14. This back and forth action of the piston creates a significant movement of membrane 18, with the frequency and amplitude of the movement depending upon the movement of piston 24 within hollow stem 14. The movement of membrane 18 creates a fluid flow in the user's mouth which cleans the teeth, including interdentally, as well as beneath the gum line.

As described above, coil assembly 28 may have two (or more) separate portions or be two (or more) separate coils. A permanent magnet may also be used. Coil assembly 28 is positioned within the toothbrush body 12 so that it is part of the toothbrush body and hence is not removed when the toothbrush stem is replaced.

Alternatively, if only a single portion coil is used, capable of moving the piston positively in only one direction, a spring (not shown) or similar member is mounted within the toothbrush stem and positioned such that when coil 28 is actuated, the piston is moved against the action of the spring. When the coil assembly is deactuated, the spring will then rebound and press the piston in the opposite direction, thereby producing, in combination with the positive action of the piston, the desired back-and-forth movement of the piston and the fluid in the hollow stem.

Figure 2A:
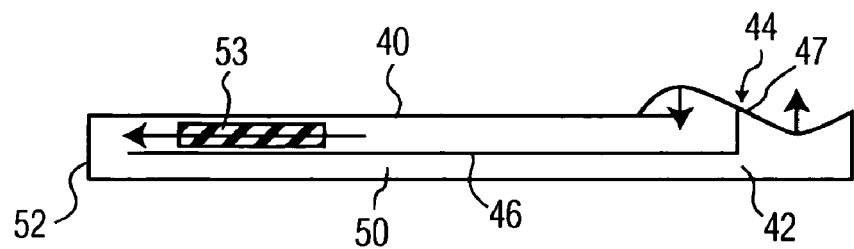
FIGS. 2A and 2B show cross-sectional and top views of another embodiment of the drive system of FIG. 1.
Figure 2B:
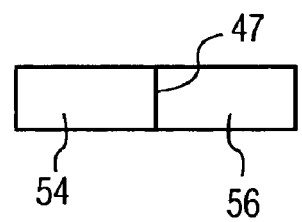

FIGS. 2A and 2B show another embodiment of the flexible membrane arrangement of the present invention. This embodiment also includes a toothbrush body, i.e. a handle (not shown) and an extending toothbrush hollow stem 40, at the remote end of which is a workpiece portion 42 in which a flexible membrane 44 is located. In this embodiment, however, stem 40 is divided longitudinally by an internal member 46 into two longitudinal separate stem sections 48 and 50. The internal member 46 terminates close to near end 52 of the stem, leaving the two stem sections 48 and 50 in fluid communication. The rear end 52 is closed off with a rigid element.

A piston 53 is positioned in one of the stem sections for alternating movement just like that for the embodiment of FIG. 1. FIG. 2B shows the top of a brushhead membrane, which is divided into two adjacent equal portions 54 and 56. The membrane 44 is fixed to the remote end 47 of internal member 46, whereby the membrane portion 54 thus can move independently of the membrane portion 56. FIG. 2B shows two rectangular portions; it should be understood, however, that that the shape of these two portions can vary, depending upon the outline of the workpiece portion 42. They could be square, for instance or semicircular or other shapes.

In operation, when piston 53 moves in one direction, membrane portion 54 will move in one direction, e.g. inwardly, while the other membrane portion 56 will move outwardly, in the opposing direction. When piston 53 moves in the other direction, the movement of the two membrane portions 54, 56 is reversed, thereby producing a sequential in-and-out, i.e. back-and-forth, alternating movement of the two membrane portions. This arrangement will produce a cleansing effect on the teeth, including interdentally, when the frequency and amplitude of the two membrane portions are within the desired ranges.

Figure 3:
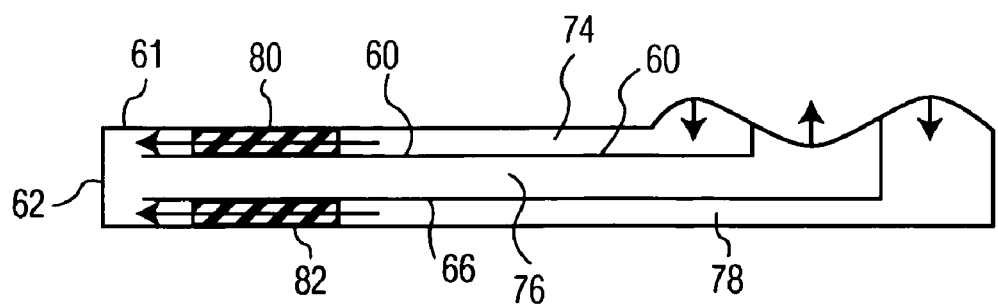
FIG. 3 shows a cross-sectional view of a further embodiment of the drive system of FIG. 1.
Figure 4A:
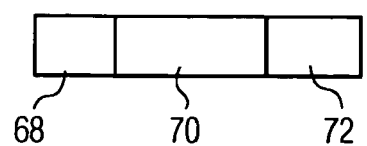
FIGS. 4A and 4B are top and cross-sectional views of one variation of the embodiment of FIG. 3.
Figure 4B:
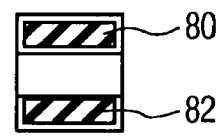

FIG. 3, as well as FIGS. 4A and 4B and 5A and 5B, show two variations of a further embodiment of the invention. This embodiment also includes a toothbrush body and a stem 60 having a near end 62 which is closed off like near end 52 of brushhead stem 40 in the embodiment of FIGS. 2A and 2B. In this arrangement, however, two internal members are used. In one variation, shown in FIGS. 4A and 4B, two separate members 60 and 66 produce a three-part membrane 67, with three sequential portions 68, 70 and 72.

In this arrangement, hollow stem 61 is divided into three separate longitudinal sections 74, 76 and 78, with fluid in each section acting on an associated membrane portion. The three longitudinal sections are in fluid communication with each other, at near end 62 thereof because members 60 and 66 do not extend all the way to end 62. The configuration of the three membrane portions can certainly differ from that shown and from each other, depending on the outline of the membrane and the position of contact between the members 60 and 66 and the membrane. Pistons 80 and 82 are provided in the outboard stem longitudinal sections 74 and 78. The two pistons 80 and 82 move together under coil action.

In operation, when the two pistons 80 and 82 move in one direction, the outboard membrane portions 68 and 70 are, for instance, moved inwardly (or outwardly), depending upon the direction of movement of the pistons. The middle membrane portion 70 will always move in the opposing direction from the movement of the outboard membrane portions, since fluid from the two outboard stem longitudinal sections 74 and 78 will be directed into or taken from the middle stem longitudinal section 78. The movement of the pistons will produce an in-and-out membrane movement, as described above, sequentially along the length thereof, in particular the outboard portions opposing the mid portion of the three-part membrane in the brushhead.

This arrangement will also produce a cleansing effect on the teeth, including interdentally, when the frequency and amplitude of the movement of the three membrane portions are within the desired ranges.

Figure 5A:
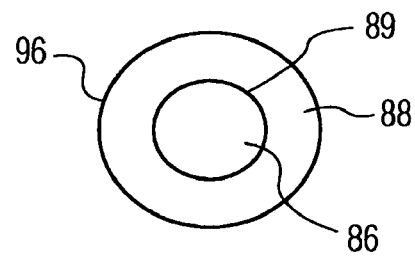
FIGS. 5A and 5B are top and cross-sectional views of another variation of the embodiment of FIG. 3.
Figure 5B:
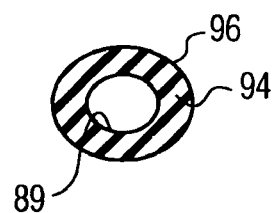

FIGS. 5A and 5B show another variation of the embodiment of FIG. 3. In this arrangement, there are two membrane portions 86 and 88 in the workpiece at the remote end of the stem 96. In the particular embodiment shown, inner membrane portion 86 is circular, while adjacent outer membrane portion 88 has a ring configuration, surrounding the inner circular membrane portion 86. An inner stem member 89 is circular, as shown in FIG. 5B. A piston 94 is also circular, fitting within the stem between outer stem 96 and inner member 89. It should be understood, however, that the membrane portions need not be circular. They can be other configurations, depending on the outline of the overall membrane and the configuration of inner stem member 89.

Movement of piston 94 in the direction of the workpiece member containing the flexible membrane will force outer membrane portion 88 outwardly, while inner membrane portion 86 will move inwardly. Alternately, with the piston moving in the other direction, the movement of membrane portions 86 and 88 will be reversed, with the outer membrane section 88 moving inwardly, while the inner membrane portion 86 will move outwardly.

This results in a slightly different membrane movement arrangement than the other embodiments described above, and may have particular cleaning effects not produced by the other variations.

It should be understood, however, that other membrane arrangements can be designed, with a stem and internal member arrangement and a piston arrangement to provide different flexible membrane movement patterns and perhaps different cleansing effects.

Although a preferred embodiment of the invention has been disclosed for purposes of illustration, it should be understood that various changes, modifications, and substitutions may be incorporated in the embodiment without departing from the spirit of the invention which is defined by the claims which follow:

The invention claimed is:

1. A power toothbrush, comprising:
a toothbrush body;
a fluid carrying stem portion extending from the toothbrush body having a membrane workpiece at a remote end thereof and a membrane at a near end thereof as well, wherein the near end membrane is separate from the membrane workpiece;
a piston assembly located in the stem portion and in direct physical contact with a fluid therein during operation, the fluid extending up to and in contact with the membrane workpiece; and
means for actuating the piston to directly move the fluid in the stem, causing at least a portion of the workpiece membrane to move outwardly when the piston moves in one direction and inwardly when the piston moves in the opposing direction.

2. The power toothbrush of claim 1, wherein the actuating means includes two or more coil portions and means for energizing the coil portions in sequence to move the piston assembly back and forth within the stem portion.

3. The power toothbrush of claim 1, wherein the actuating means includes a coil portion and a spring member, wherein the spring member is mounted within the extending portion in such a manner that when the coil is actuated, the piston is moved in one direction against the spring, and when the coil is de-actuated, the action of the spring moves the piston in the other direction, providing a back-and-forth movement of the piston and a resulting movement of the flexible membrane.

4. The power toothbrush of claim 1, wherein the actuating means is located in the toothbrush body and wherein the stem portion is removable from the toothbrush body.

5. A power toothbrush, comprising:
a toothbrush body;
a stem portion extending from the toothbrush body having a workpiece membrane at a remote end thereof, the near end of the stem being closed off by a rigid member, wherein the workpiece membrane includes more than one portion and wherein the stem portion includes at least one internal member defining two fluid channels therein, such that fluid is channeled to the separate portions of the workpiece membrane, separately, through the two fluid channels;

a piston assembly which moves within the stem in one direction so as to move fluid against at least one portion of the membrane, forcing it outwardly, and taking fluid from another portion of the membrane, drawing it inwardly and vice versa; and means for actuating the piston such that it moves alternately in opposing directions, resulting in alternating movement of at least two portions of the workpiece membrane.

6. The power toothbrush of claim 5, including more than two membrane portions.

7. The power toothbrush of claim 1, wherein a first membrane portion is circular, and a second membrane portion is ring-shaped, surrounding the circular portion.

8. The power toothbrush of claim 5, including two internal members, defining three separate stem sections within the stem portion, the toothbrush further including three membrane portions, each membrane portion responding to fluid movement in an associated stem section.

* * * * *